United States Patent [19]
Barker

[11] Patent Number: 5,569,658
[45] Date of Patent: Oct. 29, 1996

[54] TRICYCLIC DERIVATIVES

[75] Inventor: Andrew J. Barker, Macclesfield, United Kingdom

[73] Assignee: Zeneca Limited, London, United Kingdom

[21] Appl. No.: 275,754

[22] Filed: Jul. 19, 1994

[30] Foreign Application Priority Data

Jul. 19, 1993 [GB] United Kingdom ............ 9314884

[51] Int. Cl.$^6$ .............. C07D 237/26; C07D 239/70; A61K 31/495; A61K 31/505
[52] U.S. Cl. .............. 514/250; 514/252; 514/267; 544/234; 544/250; 544/251
[58] Field of Search ................ 544/234, 250, 544/251; 514/250, 252, 267

[56] References Cited

FOREIGN PATENT DOCUMENTS 0542497   5/1993   European Pat. Off. .

Primary Examiner—Matthew V. Grumbling
Attorney, Agent, or Firm—Cushman Darby & Cushman, L.L.P.

[57] ABSTRACT

The invention concerns tricyclic derivatives of the formula I

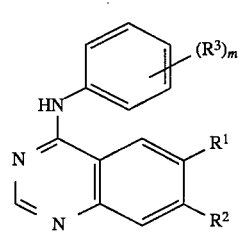

wherein $R^1$ and $R^2$ together form an optionally substituted group of the formula —N=CH—NH—, —N=CH—O—, —N=CH—S—, —N=N—NH—, —NH—N=CH—, —NH—CH=CH—. —NH—CO—NH—, —NH—CO—O—, —NH—CO—S—, —NH—NH—CO—, —N=CH—CH=N—, —N=N—CH=CH—, —N=CH—N=CH—, —N=CH—CH=N—, —NH—CO—CH=CH— or —N=CH—CO—NH—; m is 1, 2 or 3 and $R^3$ includes hydrogen, halogeno and (1–4C)alkyl; or a pharmaceutically-acceptable salt thereof;
processes for their preparation; pharmaceutical compositions containing them; and the use of the receptor tyrosine kinase inhibitory properties of the compounds. in the treatment of cancer.

15 Claims, No Drawings

TRICYCLIC DERIVATIVES

The invention relates to tricyclic derivatives, or pharmaceutically-acceptable salts thereof, which possess anti-cancer activity and are accordingly useful in methods of treatment of cancer in the human or animal body. The invention also relates to processes for the manufacture of said tricyclic derivatives, to pharmaceutical compositions containing them and to their use in the manufacture of medicaments of use in the production of an anti-cancer effect in a warm-blooded animal such as man.

Many of the current treatment regimes for cancer utilise compounds which inhibit DNA synthesis. Such compounds are toxic to cells generally but their toxic effect on the rapidly dividing tumour cells can be beneficial. Alternative approaches to anti-cancer agents which act by mechanisms other than the inhibition of DNA synthesis have the potential to display enhanced selectivity of action against cancer cells.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al. *Ann. Reports in Ned. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor and an intracellular portion which functions as a kinase to phosphorylate tyrosine amino acids in proteins and hence to influence cell proliferation. It is known that such kinases are frequently present in common human cancers such as breast cancer (Sainsbury et al., *Brit. J. Cancer*, 1988, 58, 458; Guerin et al., *Oncogene Res.*, 1988, 3, 21), gastrointestinal cancer such as colon, rectal or stomach cancer (Bolen et al., *Oncogene Res.*, 1987, 1, 149), leukaemia (Konaka et al., *Cell*, 1984, 37, 1035) and ovarian, bronchial or pancreatic cancer (European Patent Specification No. 0400586). As further human tumour tissues are tested for receptor tyrosine kinase activity it is expected that its widespread prevalence will be established in further cancers such as thyroid and uterine cancer. It is also known that tyrosine kinase activity is rarely detected in normal cells whereas it is more frequently detectable in malignant cells (Hunter, *Cell*, 1987, 50, 823). It has been shown more recently (W J Gullick, *Brit. Hed. Bull*, 1991, 47, 87) that epidermal growth factor receptor which possesses tyrosine kinase activity is overexpressed in many human cancers such as brain, lung squamous cell, bladder, gastric, breast, head and neck, oesophageal, gynaecological and thyroid tumours.

Accordingly it has been recognized that an inhibitor of receptor tyrosine kinase should be of value as a selective inhibitor of the growth of mammalian cancer cells (Yaish et al. *Science*, 1988, 242, 933). Support for this view is provided by the demonstration that erbstatin, a receptor tyrosine kinase inhibitor, specifically attenuates the growth in athymic nude mice of a transplanted human mammary carcinoma which expresses epidermal growth factor (EGF) receptor tyrosine kinase but is without effect on the growth of another carcinoma which does not express EGF receptor tyrosine kinase (Toi et al., *Eur. J. Cancer Clin. Oncol.*, 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives has been demonstrated against the growth of human squamous cell carcinoma inoculated into nude mice (Yoneda et al., *Cancer Research*, 1991, 51, 4430). Accordingly it has been indicated that receptor tyrosine kinase inhibitors will prove to be useful in the treatment of a variety of human cancers. Various known tyrosine kinase inhibitors are disclosed in a more recent review by T R Burke Jr. (*Drugs of the Future*, 1992, 17, 119).

We have now found that certain tricyclic derivatives which incorporate a quinazoline ring possess anti-cancer properties which are believed to arise from their receptor tyrosine kinase inhibitory properties.

It is known from the patent application WO 92/20642 that certain aryl and heteroaryl compounds inhibit receptor tyrosine kinase. There is the disclosure of certain quinazoline derivatives but no mention is made of 4-anilinoquinazoline derivatives.

It is also known from European Patent Application No. 92305703.8 (publication no. 0 520 722) that certain 4-anilinoquinazoline derivatives which are unsubstituted at positions 5 to 8 of the quinazoline ring or which bear a halogeno, trifluoromethyl or nitro substituent at one of those positions are useful as inhibitors of receptor tyrosine kinase.

According to the present invention there is provided a tricyclic derivative of the formula I (set out hereinafter) wherein $R^1$ and $R^2$ together form a group of the formula —N=CH—NH—, —N=CH—O—, —N=CH—S—, —N=N—NH—, —NH—N=CH—, —NH—CH=CH—, —NH—CO—NH—, —NH—CO—O—, —NH—CO—S—, —NH—NH—CO—, —N=CH—CH=CH—, —N=N—CH=CH—, —N=CH—N=CH—, —N=CH—CH=N—, —NH—CO—CH=CH— or —N=CH—CO—NH— (with in each case a nitrogen atom being located at the 6-position of the quinazoline ring) and the 5- or 6-membered ring so formed may optionally bear one or two substituents, any substituent on an available nitrogen atom being selected from (1–4C)alkyl, (3–4C)alkenyl, (3–4C)alkynyl, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-(1–4C)alkyl, (1–4C)alkylamino-(1–4C)alkyl and di-[(1–4C)alkyl]amino-(1–4C)alkyl, and any substituent on an available carbon atom being selected from halogeno, amino, hydroxy, carbamoyl, cyano, (1–4C)alkyl, (2–4C)alkenyl, (2–4C)alkynyl, (1–4C)alkoxy, (1–4C)alkylthio, (1–4C)alkylsulphinyl, (1–4C)alkylsulphonyl, (1–4C)alkylamino, di-[(1–4C)alkyl]amino, (2–4C)alkanoyl, $\underline{N}$-(1–4C)alkylcarbamoyl, $\underline{N},\underline{N}$-di-[(1–4C)alkyl]carbamoyl, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-(1–4C)alkyl, (1–4C)alkylamino-(1–4C)alkyl and di-[(1–4C)alkyl]amino-(1–4C)alkyl; and m is the integer 1, 2 or 3 and each $R^3$ is independently hydrogen, halogeno, trifluoromethyl, hydroxy, amino, nitro, cyano, (1–4C)alkyl, (1–4C)alkoxy, (1–4C)alkylamino, di-[(1–4C)alkyl]amino or (2–4C)alkanoylamino; or a pharmaceutically-acceptable salt thereof.

The chemical formulae referred to herein by Roman numerals are set out for convenience on a separate sheet hereinafter. In this specification the term "alkyl" includes both straight and branched chain alkyl groups but references to individual alkyl groups such as "propyl" are specific for the straight chain version only. An analogous convention applies to other generic terms.

Within the present invention it is to be understood that a quinazoline of the formula I may exhibit the phenomenon of tautomerism and that the formulae drawings within this specification can represent only one of the possible tautomeric forms. It is to be understood that the invention encompasses any tautomeric form which possesses anti-cancer activity and is not to be limited merely to any one tautomeric form utilised within the formulae drawings.

The quinazolines of the formula I are unsubstituted at the 2-, 5- and 8-positions.

It is also to be understood that certain quinazolines of the formula I can exist in solvated as well as unsolvated forms such as, for example, hydrated forms. It is to be understood that the invention encompasses all such solvated forms which possess anti-cancer activity.

According to a further aspect of the present invention there is provided a tricyclic derivative of the formula I wherein $R^1$ and $R^2$ together form a group of the formula —N=CH—NH—, —N=CH—O—, —N=CH—S—, —N=N—NH—, —NH—N=CH—, —NH—CH=CH—, —NH—CO—NH—, —NH—CO—, —NH—CO—S—, —NH—NH—CO—, —N=CH—CH=CH—, —N=N—CH=CH—, —N=CH—N=CH—, —N=CH—CH=N— or —NH—CO—CH=CH— (with in each case a nitrogen atom being located at the 6-position of the quinazoline ring) and the 5- or 6-membered ring so formed may optionally bear one or two substituents, any substituent on an available nitrogen atom being selected from (1–4C)alkyl, (3–4C)alkenyl, (3–4C)alkynyl, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-(1–4C)alkyl, (1–4C)alkylamino-(1–4C)alkyl and di-[(1–4C)alkyl]amino-(1–4C)alkyl, and any substituent on an available carbon atom being selected from halogeno, amino, carbamoyl, cyano, (1–4C)alkyl, (2–4C)alkenyl, (2–4C)alkynyl, (1–4C)alkoxy, (1–4C)alkylthio, (1–4C)alkylsulphinyl, (1–4C)alkylsulphonyl, (1–4C)alkylamino, di-[(1–4C)alkyl]amino, (2–4C)alkanoyl, N-(1–4C)alkylcarbamoyl, N,N-di-[(1–4C)alkyl]carbamoyl, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-(1–4C)alkyl, (1–4C)alkylamino-(1–4C)alkyl and di-[(1–4C)alkyl]amino-(1–4C)alkyl; and m is the integer 1, 2 or 3 and each $R^3$ is independently hydrogen, halogeno, trifluoromethyl, hydroxy, amino, nitro, cyano, (1–4C)alkyl, (1–4C)alkoxy, (1–4C)alkylamino, di-[(1–4C)alkyl]amino or (2–4C)alkanoylamino; or a pharmaceutically-acceptable salt thereof.

Suitable values for the generic radicals referred to above include those set out below.

Suitable values for each substituent which may be present on the ring involving $R^1$ and $R^2$ or for each $R^3$ substituent which may be present include, for example:
for halogeno: fluoro, chloro, bromo and iodo;
for (1–4C)alkyl: methyl, ethyl, propyl, isopropyl, butyl, isobutyl, sec-butyl and tert-butyl;
for (3–4C)alkenyl: allyl and but-2-enyl;
for (2–4C) alkenyl: vinyl, allyl and but-2-enyl;
for (3–4C)alkynyl: prop-2-ynyl and but-2-ynyl;
for (2–4C)alkynyl: ethynyl, prop-2-ynyl and but-2-ynyl;
for (1–4C)alkoxy: methoxy, ethoxy, propoxy, isopropoxy and butoxy;
for (1–4C)alkylthio: methylthio, ethylthio and propylthio;
for (1–4C)alkylsulphinyl: methylsulphinyl, ethylsulfinyl and propylsulphinyl;
for (1–4C)alkylsulphonyl: methylsulphonyl, ethylsulphonyl and propylsulphonyl;
for (1–4C)alkylamino: methylamino, ethylamino and propylamino;
for di-[(1–4C)alkyl]amino: dimethylamino, N-ethyl-N-methylamino, diethylamino, N-methyl-N-propylamino and dipropylamino;
for (2–4C)alkanoylamino: acetamido, propionamido and butyramido;
for (2–4C)alkanoyl: acetyl, propionyl and butyryl;
for N-(1–4C)alkylcarbamoyl: N-methylcarbamoyl, N-ethylcarbamoyl and N-propylcarbamoyl;
for N,N-di-[(1–4C)alkyl]-carbamoyl: N,N-dimethylcarbamoyl, N-ethyl-N-methylcarbamoyl and N,N-diethylcarbamoyl;
for halogeno-(1–4C)alkyl: fluoromethyl, chloromethyl, bromomethyl, difluoromethyl, dichloromethyl, dibromomethyl, 2-fluoroethyl, 2,2-difluoroethyl, 2,2,2-trifluoroethyl, 2-chloroethyl, 2-bromoethyl and trifluoromethyl;
for hydroxy-(1–4C)-alkyl: hydroxymethyl, 1-hydroxyethyl, 2-hydroxyethyl and 3-hydroxypropyl;
for (2–4C)alkanoyloxy-(1–4C)-alkyl: acetoxymethyl, propionyloxymethyl, butyryloxymethyl, 2-acetoxyethyl and 3-acetoxypropyl;
for (1–4C)alkoxy-(1–4C)alkyl: methoxymethyl, ethoxymethyl, 1-methoxyethyl, 2-methoxyethyl, 2-ethoxyethyl and 3-methoxypropyl;
for cyano-(1–4C)alkyl: cyanomethyl, 1-cyanoethyl, 2-cyanoethyl and 3-cyanopropyl;
for amino-(1–4C)alkyl: aminomethyl, 1-aminoethyl, 2-aminoethyl and 3-aminopropyl;
for (1–4C)alkylamino-(1–4C)-alkyl: methylaminomethyl, ethylaminomethyl, 1-methylaminoethyl, 2-methylaminoethyl, 2-ethylamimoethyl and 3-methylaminopropyl; for di-[(1–4C)alkyl]amino-(1–4C)alkyl: dimethylaminomethyl, diethylaminomethyl, 1-dimethylaminoethyl, 2-dimethylaminoethyl and 3-dimethylaminopropyl.

A suitable pharmaceutically-acceptable salt of a tricyclic derivative of the invention is, for example, an acid-addition salt of a tricyclic derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a tricyclic derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, tricyclic derivatives of the formula I, or pharmaceutically-acceptable salts thereof wherein:
(a) the optionally-substituted tricyclic ring defined by the linking of the $R^1$ and $R^2$ substituents on the quinazoline of the formula I is selected from 3H-imidazo[4,5-g]quinazolin-8-yl, oxazolo[4,5-g]quinazolin-8-yl, thiazolo[4,5-g]quinazolin-8-yl, 3H-[1,2,3]triazolo[4,5-g]quinazolin-8-yl, 1H-pyrazolo[3,4-g]quinazolin-8-yl, 6H-pyrrolo[2,3-g]quinazolin-4-yl, 2-oxo-1,2-dihydro-3H-imidazo[4, 5-g]quinazolin-8-yl, 2-oxo-1,2-dihydrooxazolo[4,5-g] quinazolin-8-yl, 2-oxo-1,2-dihydrothiazolo[4,5-g] quinazolin-8-yl and 3-oxo-2,3-dihydro-1H-pyrazolo[3,4-g]quinazolin-8-yl; and m and $R^3$ have any of the meanings defined hereinbefore;

(b) the optionally-substituted tricyclic ring defined by the linking of the $R^1$ and $R^2$ substituents on the quinazoline of the formula I is selected from pyrido[2,3-g]quinazolin-4-yl, pyrimidino[4,5-g]cinnolin-9-yl, pyrimidino[4,5-g]quinazolin-4-yl, pyrazino[2,3-g]quinazolin-4-yl and 7-oxo-6,7-dihydropyrido[2,3-g]quinazolin-4-yl; and m and $R^3$ have any of the meanings defined hereinbefore; or (c) the optionally-substituted tricyclic ring defined by the linking of the $R^1$ and $R^2$ substituents on the quinazoline of the formula I is selected from pyrazino[2,3-g]quinazolin-4-yl and 8-oxo-8,9-dihydropyrazino[2,3-g]quinazolin-4-yl; and m and $R^3$ have any of the meanings defined hereinbefore.

A further particular compound of the invention is a tricyclic derivative of the formula I
wherein the 6,6,5-tricyclic ring defined by the linking of the groups $R^1$ and $R^2$ is selected from 3H-imidazo[4,5-g]quinazolin-8-yl, oxazolo[4,5-g]quinazolin-8-yl, thiazolo[4,5-g]quinazolin-8-yl, 3H-[1,2,3]triazolo[4,5-g]quinazolin-8-yl, 1H-pyrazolo[3,4-g]quinazolin-8-yl, 6H-pyrrolo[2,3-g]quinazolin-4-yl, 2-oxo-1,2-dihydro-3-imidazo[4,5-g]quinazolin-8-yl, 2-oxo-1,2-dihydrooxazolo[4,5-g]quinazolin-8-yl, 2-oxo-1,2-dihydrothiazolo[4,5-g]quinazolin-8-yl and 3-oxo-2,3-dihydro-1H-pyrazolo[3,4-g]quinazolin-8-yl, and the 5-membered ring involving $R^1$ and $R^2$ may optionally bear one or two substituents, any substituent on an available nitrogen atom being selected from methyl, ethyl, propyl, allyl, prop-2-ynyl, 2,2,2-trifluoroethyl, 2-hydroxyethyl, 3-hydroxypropyl, 2-acetoxyethyl, 2-methoxyethyl, 3-methoxypropyl, cyanomethyl, 2-cyanoethyl, 2-aminoethyl, 2-methylaminoethyl and 2-dimethylaminoethyl, and any substituent on an available carbon atom being selected from fluoro, chloro, amino, carbamoyl, cyano, methyl, ethyl, propyl, vinyl, allyl, ethynyl, prop-2-ynyl, methoxy, ethoxy, propoxy, methylthio, methylsulphinyl, methylsulphonyl, methylamino, dimethylamino, acetyl, N-methylcarbamoyl, N,N-dimethylcarbamoyl, fluoromethyl, difluoromethyl, trifluoromethyl, 2,2,2-trifluoroethyl, hydroxymethyl, 2-hydroxyethyl, acetoxymethyl, 2-acetoxyethyl, methoxymethyl, 2-methoxyethyl, cyanomethyl, 2-cyanoethyl, aminomethyl, 2-aminoethyl, methylaminomethyl, 2-methylaminoethyl, dimethylaminomethyl and 2-dimethylaminoethyl; and m is the integer 1, 2 or 3 and each $R^3$ is independently hydrogen, fluoro, chloro, bromo, trifluoromethyl, hydroxy, amino, nitro, cyano, methyl, ethyl, methoxy, methylamino, dimethylamino or acetamido; or a pharmaceutically-acceptable salt thereof.

A further particular compound of the invention is a tricyclic derivative of the formula I
wherein the 6,6,6-tricyclic ring defined by the linking of the groups $R^1$ and $R^2$ is selected from pyrido[2,3-g]quinazolin-4-yl, pyrimidino[4,5-g]cinnolin-9-yl, pyrimidino[4,5-g]quinazolin-4-yl, pyrazino[2,3-g]quinazolin-4-yl, 7-oxo-6,7-dihydropyrido[2,3-g]quinazolin-4-yl and 8-oxo-8,9-dihydropyrazino[2,3-g]quinazolin-4-yl, and the 6-membered ring involving $R^1$ and $R^2$ may optionally bear one two substituents, any substituent on an available nitrogen atom being selected from methyl, ethyl and propyl, and any substituent on an available carbon atom being selected from fluoro, chloro, hydroxy, carbamoyl, cyano, methyl, methoxy, ethoxy, N-methylcarbamoyl, N,N-dimethylcarbamoyl, trifluoromethyl and 2,2,2-trifluoroethyl; and m is the integer 1 or 2 and each $R^3$ is independently hydrogen, fluoro, chloro, bromo, trifluoromethyl, nitro, cyano, methyl or ethyl; or a pharmaceutically-acceptable salt thereof.

A preferred compound of the invention is a tricyclic derivative of the formula I
wherein the 6,6,5-tricyclic ring defined by the linking of the groups $R^1$ and $R^2$ is selected from 3-methyl-3-imidazo[4,5-g]quinazolin-8-yl, 3-methyl-3H-[1,2,3]triazolo[4,5-g]quinazolin-8-yl and 3-methyl-2-oxo-1,2-dihydro-3H-imidazo[4,5-g]quinazolin-8-yl; and $(R^3)_m$ is 3'-methyl, 3'-chloro or 3'-chloro-4'-fluoro; or a pharmaceutically-acceptable salt thereof.

A further preferred compound of the invention is a tricyclic derivative of the formula I
wherein the 6,6,5-tricyclic ring defined by the linking of the groups $R^1$ and $R^2$ is selected from 3-methyl-3H-imidazo[4,5-g]quinazolin-8-yl, 3-methyl-2-oxo-1,2-dihydro-3H-imidazo[4,5-g]quinazolin-8-yl and 3-methyl-2-trifluoromethyl-3H-imidazo[4,5-g]quinazolin-8-yl; and $(R^3)_m$ is 3'-methyl, 3'-chloro or 3'-chloro-4'-fluoro; or a pharmaceutically-acceptable salt thereof.

A further preferred compound of the invention is a tricyclic derivative of the formula I
wherein the 6,6,6-tricyclic ring defined by the linking of the groups $R^1$ and $R^2$ is selected from 7,8-dimethylpyrazino[2,3-g]quinazolin-4-yl and 7-hydroxy-9-methyl-8-oxo-8,9-dihydropyrazino[2,3-g]quinazolin-4-yl; and $(R^3)_m$ is 3'-methyl, 3'-chloro or 3'-chloro-4'-fluoro or a pharmaceutically-acceptable salt thereof.

A specific preferred compound of the invention is the following tricyclic derivative of the formula I: 3-methyl-8-(3'-methylanilino)-3H-imidazo[4,5-g]quinazoline, 3-methyl-8-(3'-methylanilino)-1,2-dihydro-3H-imidazo[4,5-g]quinazolin-2-one or 8-(3'-chloro-4'-fluoroanilino)-3-methyl-2-trifluoromethyl-3[-imidazo-[4,5-g]quinazoline; or a pharmaceutically-acceptable salt thereof.

A further specific preferred compound of the invention is the following tricyclic derivative of the formula I:
4-(3'-chloro-4'-fluoroanilino)-7,8-dimethylpyrazino[2,3-g]quinazoline or 4-(3'-chloro-4'-fluoroanilino)-7-hydroxy-9-methyl-8-oxo-8,9-dihydropyrazino[2,3-g]quinazoline;
or a pharmaceutically-acceptable salt thereof.

A tricyclic derivative of the formula I, or a pharmaceutically-acceptable salt thereof, may be prepared by any process known to be applicable to the preparation of chemically-related compounds. A suitable process is, for example, illustrated by that used in European Patent Application No. 0 520 722. Such processes, when used to prepare a tricyclic derivative of the formula I, or a pharmaceutically-acceptable salt thereof, are provided as a further feature of the invention and are illustrated by the following representative examples in which, unless otherwise stated, $R^1$, $R^2$, $R^3$ and m have any of the meanings defined hereinbefore for a tricyclic derivative of the formula I. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(a) The reaction, conveniently in the presence of a suitable base, of a quinazoline of the formula II (set out hereinafter), wherein Z is a displaceable group, with an aniline of the formula III.

A suitable displaceable group Z is, for example, a halogeno, alkoxy, aryloxy or sulphonyloxy group, for example a chloro, bromo, methoxy, phenoxy, methanesulphonyloxy or toluene-p-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide. Alternatively a suitable base is, for example, an alkali metal or alkaline earth metal amide, for example sodium amide or sodium bis(trimethylsilyl)amide.

The reaction is preferably carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10° to 150° C., preferably in the range 20° to 80° C.

The quinazoline derivative of the formula I may be obtained from this process in the form of the free base or alternatively it may be obtained in the form of a salt with the acid of the formula H-Z wherein Z has the meaning defined hereinbefore. When it is desired to obtain the free base from the salt, the salt may be treated with a suitable base as defined hereinbefore using a conventional procedure.

(b) For the production of those optionally-substituted compounds of the formula I wherein $R^1$ and $R^2$ together form a group of the formula —N=CH—NH— or —NH—CO—NH—, the cyclisation of a compound of the formula I wherein $R^1$ is amino and $R^2$ is amino, (1–4C)alkylamino, (3–4C)alkenylamino, (3–4C)alkynylamino or a substituted-(1–4C)alkylamino with an appropriate carboxylic acid, an amide of a carboxylic acid, a urea or a carbonate.

The reaction is conveniently performed in the presence of a suitable inert solvent or diluent as defined hereinbefore and at a temperature in the range, for example, 10° to 150° C, preferably in the range 60° to 120° C.

(c) For the production of those optionally-substituted compounds of the formula I wherein $R^1$ and $R^2$ together form a group of the formula —N=N—NH—, the diazotisation and cyclisation of a compound of the formula I wherein $R^1$ is amino and $R^2$ is amino, (1–4C)alkylamino, (3–4C)alkenylamino, (3–4C)alkynylamino or a substituted-(1–4C)alkylamino.

A suitable diazotisation reagent is, for example, an alkali metal or alkaline earth metal nitrite, for example sodium nitrite, in the presence of a suitable acid such as sulphuric acid.

The reaction is conveniently performed at a temperature in the range, for example, −10° to +50° C., preferably in the range 0° to 30° C.

(d) For the production of those optionally-substituted compounds of the formula I wherein $R^1$ and $R^2$ together form a group of the formula —N=CH—CH=N—, the cyclisation of a compound of the formula I wherein $R^1$ is amino and $R^2$ is amino with an appropriate diketone.

The reaction is conveniently performed in the presence of a suitable inert solvent or diluent as described hereinbefore and at a temperature in the range, for example, 10° to 150° C., preferably in the range 50° to 100° C.

(e) For the production of those optionally-substitute compounds of the formula I wherein $R^1$ and $R^2$ together form a group of the formula —N=CH—CO—NH—, the cyclisation of a compound of the formula I wherein $R^1$ is amino and $R^2$ is amino, (1–4C)alkylamino, (3–4C)alkenylamino, (3–4C)alkynylamino or a substituted-(1–4C)alkylamino with an appropriate dicarboxylic acid or di-ester thereof.

The reaction is conveniently performed in the presence of a suitable inert solvent or diluent, as defined hereinbefore and at a temperature in the range, for example, 10° to 150° C., preferably in the range 50° to 100° C.

(f) For the production of those compounds of the formula I which bear a (1–4C)alkylsulphinyl or (1–4C)alkylsulphonyl substituent, the oxidation of a quinazoline derivative of the formula I which bears a (1–4C)alkylthio substituent.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, −25° to 50° C., conveniently at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a (1–4C)alkylsulphonyl group is required, it may be obtained by oxidation of the corresponding (1–4C)alkylsulphinyl compound as well as of the corresponding (1–4C)alkylthio compound.

When a pharmaceutically-acceptable salt of a tricyclic derivative of the formula I is required, for example an acid-addition salt of a tricyclic derivative of the formula I, it may be obtained, for example, by reaction of said compound with, for example, a suitable acid using a conventional procedure.

As stated hereinbefore the tricyclic derivative defined in the present invention possesses anti-cancer activity which is believed to arise from the receptor tyrosine kinase inhibitory activity of the compound. These properties may be assessed, for example, using one or more of the procedures set out below:

(a) An in vitro assay which determines the ability of a test compound to inhibit the enzyme receptor tyrosine kinase. Receptor tyrosine kinase was obtained in partially purified form from A-431 cells (derived from human vulval carcinoma) by procedures related to those described by Carpenter et al., *J. Biol. Chem.*, 1979, 254, 4884, Cohen et al., *J. Biol. Chem.*, 1982, 257, 1523 and by Braun et al., *J. Biol. Chem.*, 1984, 259, 2051.

A-431 cells were grown to confluence using Dulbecco's modified Eagle's medium (DMEM) containing 5% fetal calf serum (FCS). The obtained cells were homogenised in a hypotonic borate/EDTA buffer at pH 10.1. The homogenate was centrifuged at 400 g for 10 minutes at 0°–4° C. The supernatant was centrifuged at 25,000 g for 30 minutes at 0°–4° C. The pelleted material was suspended in 30 mM Hepes buffer at pH 7.4 containing 5% glycerol, 4 mM benzamidine and 1% Triton X-100, stirred for 1 hour at 0–4° C., and recentrifuged at 100,000 g for 1 hour at 0°–4° C. The supernatant, containing solubilised receptor tyrosine kinase, was stored in liquid nitrogen.

For test purposes 40 µl of the enzyme solution so obtained was added to a mixture of 400 µl of a mixture of 150 mM Hepes buffer at pH 7.4, 500 µM sodium orthovanadate, 0.1% Triton X-100, 10% glycerol, 200 µl water, 80 µl of 25 mM DTT and 80 µl of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 µM solution. Equal volumes of this solution and a solution of epidermal growth factor (EGF; 20 µg/ml) were mixed.

[γ-$^{32}$P]ATP (3000 Ci/mM, 250 µCi) was diluted to a volume of 2 ml by the addition of a solution of ATP (100 µM) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mM Hepes buffer at pH 7.4, 0.1% Triton X-100 and 10% glycerol was added.

The test compound/EGF mixture solution (5 µl) was added to the test enzyme solution (10 µl) and the mixture was incubated at 0°–4° C. for 30 minutes. The ATP/peptide mixture (10 µl) was added and the mixture was incubated at 25° C. for 10 minutes. The phosphorylation reaction was terminated by the addition of 5% trichloroacetic acid (40 µl) and bovine serum albumin (BSA; 1 mg/ml, 5 µl). The mixture was allowed to stand at 4° C. for 30 minutes and then centrifuged. An aliquot (40 µl) of the supernatant was placed onto a strip of Whatman p 81 phosphocellulose paper. The strip was washed in 75 mM phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an IC$_{50}$ value.

(b) An in vitro assay which determines the ability of a test compound to inhibit the growth of the human nasopharyngeal cancer cell line KB.

KB cells were seeded into wells at a density of 1×10$^4$–1.5×10$^4$ cells per well and grown for 24 hours in DMEM supplemented with 5% FCS (charcoal-stripped). Cell growth was determined after incubation for 3 days by the extent of metabolism of MTT tetrazolium dye to furnish a bluish color. Cell growth was then determined in the presence of EGF (10 ng/ml) or in the presence of EGF (10 ng/ml) and a test compound at a range of concentrations. An IC$_{50}$ value could then be calculated.

(c) An in vivo assay in a group of male rats which determines the ability of a test compound (usually administered orally as a ball-milled suspension in 0.5% polysorbate) to inhibit the stimulation of liver hepatocyte growth caused by the administration of the growth factor TGFα (400 µg/kg subcutaneously, usually dosed twice, 3 and 7 hours respectively after the administration of the test compound).

In a control group of rats, the administration of TGFα causes on average a 5-fold stimulation of liver hepatocyte growth.

Cell-growth in the control and test animals is determined as follows:

On the morning of the day after the dosing of the test compound (or 0.5% polysorbate in the control group), the animals are dosed with bromodeoxyuridine (BrdU; 100 mg/kg intraperitoneally). The animals are killed four hours later and the livers are excised. Slices are cut from each liver and the uptake of BrdU is determined by a conventional immunohistochemical technique similar to that described on pages 267 and 268 of an article by Goldsworthy et al. in Chemically Induced Cell Proliferation: Implications for Risk Assessment, Wiley-Liss Inc., 1991, pages 253–284. Further tests were carried out using a range of doses of the test compounds to allow the calculation of an approximate ED$_{50}$ value for the inhibition of liver hepatocyte proliferation as determined by inhibition of the uptake of BrdU.

Although the pharmacological properties of the compounds of the formula I vary with structural change as expected, in general activity possessed by compounds of the formula I may be demonstrated at the following concentrations or doses in one or more of the above tests (a), (b) and (c):

Test (a): IC$_{50}$ in the range, for example, 0.0005–1 µM;

Test (b): IC$_{50}$ in the range, for example, 0.01–10 µM;

Test (c): ED$_{50}$ in the range, for example, 1–100 mg/kg.

Thus, by way of example, the compound 3-methyl-8-(3'-methylanilino)-3H-imidazo[4,5-g]quinazoline has an IC$_{50}$ of 0.035 µM in Test (a), an IC$_{50}$ of 0.97 µM in Test (b) and an ED$_{50}$ of <5 mg/kg in Test (c); and the compound 3-methyl-8-(3'-methylanilino)-1,2-dihydro-3H-imidazo[4,5-g]quinazolin-2-one has an IC$_{50}$ of 0.016 µM in Test (a), an IC$_{50}$ of 1.19 µM in Test (b) and an ED$_{50}$ of <12.5 mg/kg in Test (c).

According to a further aspect of the invention there is provided a pharmaceutical composition which comprises a tricyclic derivative of the formula I, or a pharmaceutically-acceptable salt thereof, as defined hereinbefore in association with a pharmaceutically-acceptable diluent or carrier.

The composition may be in a form suitable for oral administration, for example as a tablet or capsule, for parenteral injection (including intraveous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a tricyclic derivative of the formula I as defined hereinbefore for use in a method of treatment of the human or animal body by therapy.

We have now found that the compounds of the present invention possess anti-cancer properties which are believed to arise from their receptor tyrosine kinase inhibitory activity. Accordingly the compounds of the present invention are expected to be useful in the treatment of diseases or medical conditions mediated alone or in part by the enzyme receptor tyrosine kinase, i.e. the compounds may be used to produce a receptor tyrosine kinase inhibitory effect in a warm-blooded animal in need of such treatment. Thus the compounds of the present invention provide a method for treating the proliferation of malignant cells characterised by inhibition of the enzyme receptor tyrosine kinase, i.e. the compounds may be used to produce an anti-proliferative effect mediated alone or in part by the inhibition of the enzyme receptor tyrosine kinase. Accordingly the compounds of the present invention are expected to be useful in the treatment of cancer by providing an anti-proliferative effect, particularly in the treatment of receptor tyrosine kinase sensitive cancers such as cancers of the breast, lung, colon, rectum, stomach, prostate, bladder, pancreas and ovary.

Thus according to this aspect of the invention there is provided the use of a tricyclic derivative of the formula I, or a pharmaceutically-acceptable salt thereof, as defined hereinbefore in the manufacture of a medicament for use in the production of an anti-cancer effect in a warm-blooded animal such as man.

According to a further feature of this aspect of the invention there is provided a method for producing an anti-cancer effect in a warm-blooded animal, such as man, in need of such treatment which comprises administering to said animal an effective amount of a tricyclic derivative as defined immediately above.

As stated above the size of the dose required for the therapeutic or prophylactic treatment of a particular cancer will necessarily be varied depending on the host treated, the route of administration and the severity of the illness being treated. A unit dose in the range, for example, 1–100 mg/kg, preferably 1–50 mg/kg is envisaged.

The anti-cancer treatment defined hereinbefore may be applied as a sole therapy or may involve, in addition to the quinazoline derivative of the invention, one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred antimetabolites disclosed in European Patent Application No. 239362 such as N-{5-[N-(3,4-dihydro-2-methyl-4-oxoquinazolin-6-ylmethyl)-N-methylamino]-2-thenoyl}-L-glutamic acid; intercalating antibiotics, for example adriamycin and bleomycin; enzymes, for example asparaginase; topoisomerase inhibitors, for example etoposide; biological response modifiers, for example interferon; and anti-hormones, for example antioestrogens such as 'NOLVADEX' (tamoxifen) or, for example antiandrogens such as 'CASODEX' (4'-cyano-3-(4-fluorophenylsulphonyl)-2-hydroxy-2-methyl-3'-(trifluoromethyl)propionanilide. Such conjoint treatment may be achieved by way of the simultaneous, sequential or separate dosing of the individual components of the treatment. According to this aspect of the invention there is provided a pharmaceutical product comprising a tricyclic derivative of the formula I as defined hereinbefore and an additional anti-tumour substance as defined hereinbefore for the conjoint treatment of cancer.

As stated above the tricyclic derivative defined in the present invention is an effective anti-cancer agent, which property is believed to arise from its receptor tyrosine kinase inhibitory properties. Such a tricyclic derivative of the invention is expected to possess a wide range of anti-cancer properties as receptor tyrosine kinases have been implicated in many common human cancers such as leukemia and breast, lung colon, rectal, stomach, prostate, bladder, pancreas and ovarian cancer. Thus it is expected that a tricyclic derivative of the invention will possess anti-cancer activity against these cancers. It is in addition expected that a tricyclic derivative of the present invention will possess activity against a range of leukaemias, lymphoid malignancies and solid tumours such as carcinomas and sarcomas in tissues such as the liver, kidney, prostate and pancreas.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet;

(vii) intermediates were not generally fully characterised and purity was assessed by thin layer chromatography (TLC), infra-red (IR) or NMR analysis;

(viii) the following abbreviations have been used:
DMF N,N-dimethylformamide;
DMA N,N-dimethylacetamide.

EXAMPLE 1

A mixture of 6-amino-7-methylamino-4-(3'-methylanilino)-quinazoline (0.61 g) and formic acid (50 ml) was stirred and heated to reflux for 1 hour. The mixture was evaporated and the residue was triturated under a dilute aqueous ammonium hydroxide solution. The resultant solid was isolated, washed with water and dried. There was thus obtained 3-methyl-8-(3'-methylanilino)-3H-imidazo[4,5-g]- quinazoline (0.59 g), m.p. >290° C.;

NMR Spectrum: (CD$_3$SOCD$_3$) 2.36 (s, 3H), 3.95 (s, 3H), 6.94 (d, 1H), 7.28 (m, 1H), 7.75 (m, 2H), 7.93 (s, 1H), 8.50 (s, 1H), 8.55 (s, 1H), 9.06 (s, 1H), 9.72 (broad s, 1H);

Elemental Analysis: Found C, 66.7; H, 5.4; N, 22.9; C$_{17}$H$_{15}$N$_5$ 1H$_2$O requires C, 66.4; H, 5.5; N, 22.8%.

The 6-amino-7-methylamino-4-(3'-methylanilino) quinazoline used as a starting material was obtained as follows:

A mixture of 4-chloroanthranilic acid (17.2 g) and formamide (10 ml) was stirred and heated to 130° C. for 45 minutes and to 175° C. for 75 minutes. The mixture was allowed to cool to approximately 100° C. and 2-(2-ethoxyethoxy)ethanol (50 ml) was added. The solution so formed was poured into a mixture (250 ml) of ice and water. The precipitate was isolated, washed with water and dried. There was thus obtained 7-chloroquinazolin-4-one (15.3 g, 85%).

A portion (6 g) of the material so obtained was added portionwise to a stirred mixture of concentrated sulphuric acid (12 ml) and fuming nitric acid (12 ml). The mixture was heated to 110° C. for 30 minutes. The mixture was cooled to ambient temperature and poured onto ice. The solid was isolated, washed with water and dried. There was thus obtained 7-chloro-6-nitroquinazolin-4-one (6.89 g, 92%).

A mixture of a portion (4 g) of the material so obtained, thionyl chloride (30 ml), phosphoryl chloride (5 ml) and DMF (10 drops) was stirred and heated to reflux for 4 hours. The mixture was evaporated. A mixture of the residue, 3'-methylaniline (1.89 g) and isopropanol (25 ml) was stirred and heated to reflux for 2 hours. The mixture was filtered and the solid was washed with isopropanol and with diethyl ether. There was thus obtained 7-chloro-4-(3'-methylanilino)-6-nitroquinazoline (3.74 g, 67%), m.p. 271°–274° C.

NMR Spectrum: (CD$_3$SOCD$_3$) 2.37 (s, 3H), 7.13 (d, 1H), 7.47 (t, 1H), 7.57 (m, 2H), 8.20 (s, 1H), 8.83 (s, 1H), 9.72 (s, 1H).

After repetition of the previous steps, a mixture of 7-chloro-4-(3'-methylanilino)-6-nitroquinazoline (10.5 g), an ethanolic solution of methylamine (30% weight/volume; 100 ml) and ethanol (100 ml) was stirred at ambient temperature for 16 hours. The mixture was evaporated to give 7-methylamino-4-(3'-methylanilino)-6-nitroquinazoline which was used without further purification.

A mixture of 7-methylamino-4-(3'-methylanilino)-6-nitroquinazoline (0.7 g), 10% palladium-on-charcoal catalyst (0.07 g) and ethanol (100 ml) was stirred and heated to 45° C. under an atmosphere of hydrogen for 2 hours. The mixture was cooled to ambient temperature and filtered. The filtrate was evaporated and the residue was purified by column chromatography using increasingly polar mixtures of methylene chloride and methanol as eluent. There was thus obtained 6-amino-7-methylamino-4-(3'-methylanilino) quinazoline (0.71 g) as a gum.

EXAMPLE 2

A mixture of 6-amino-7-methylamino-4-(3'-methylanilino)-quinazoline (0.2 g), urea (0.266 g) and DMA (8 ml) was stirred and heated to reflux for 2 hours. The mixture was evaporated and the residue was triturated under water. The resultant solid was isolated, washed with water and dried. The residue was dissolved in a mixture of DHSO (1 ml) and methanol (2 ml). The solution was acidified to pH1 by the addition of trifluoroacetic acid. The precipitate was isolated, washed with water, with acetone and with diethyl ether and dried. There was thus obtained 3-methyl-8-(3'-methylanilino)-1,2-dihydro-3H-imidazo[4,5-g]quinazolin-2-one (0.128 g);

NMR Spectrum: (CD$_3$SOCD$_3$) 3.38 (s, 3H), 3.40 (s, 3H), 7.11 (d, 1H), 7.36 (m, 1H), 7.39 (s, 1H), 7.50 (d, 1H), 7.52 (s, 1H), 8.24 (s, 1H), 8.79 (s, 1H), 10.9 (broad s, 1H), 11.95 (broad s, 1H);

Elemental Analysis: Found C, 54.6; H, 3.8; N, 16.7; C$_{17}$H$_{15}$N$_5$O 1CF$_3$CO$_2$H requires C, 54.4; H, 3.8; N, 16.7%.

EXAMPLE 3

A solution of sodium nitrite (0.065 g) in water (1 ml) was added dropwise during 5 minutes to a stirred suspension of 6-amino-4-(3'-chloro-4'-fluoroanilino)-7-methylaminoquinazoline (0.3 g) in 2N aqueous sulphuric acid solution (10 ml) which had been cooled to 0° C. The mixture was stirred at 0° C. for 5 minutes, allowed to warm to ambient temperature and stirred for 20 minutes. The mixture was basified to pH10 by the addition of a concentrated aqueous ammonium hydroxide solution. The precipitate was isolated and triturated under methanol (10 ml). The solid was isolated, washed with methanol and with diethyl ether and dried. There was thus obtained 8-(3'-chloro-4'-fluoroanilino)-3-methyl-3H-[1,2,3]triazolo[4,5-g]quinazoline (0.177 g);

NMR Spectrum: (CD$_3$SOCD$_3$) 4.43 (s, 3H), 7.47 (m, 1H), 7.92 (m, 1H), 8.24 (s, 1H), 8.31 (m, 1H), 8.65 (s, 1H), 9.48 (s, 1H), 10.26 (broad s, 1H);

Elemental Analysis: Found C, 54.2; H, 3.0; N, 24.4; C$_{15}$H$_{10}$N$_6$ClF 0.45CH$_3$OH requires C, 54.0; H, 3.4; N, 24.5%.

The 6-amino-4-(3'-chloro-4'-fluoroanilino)-7-methylaminoquinazoline used as a starting material was obtained as follows:

A mixture of 7-chloro-6-nitroquinazolin-4-one (30 g), thionyl chloride (300 ml) and DMF (0.5 ml) was stirred and heated to reflux for 5 hours. The mixture was evaporated, toluene (50 ml) was added and he solution was evaporated. A mixture of the residue, 3-chloro-4-fluoroaniline (19.5 g) and isopropanol (100 ml) was stirred and heated to reflux for 2 hours. The mixture was cooled to ambient temperature. The precipitate was isolated and washed with isopropanol and with diethyl ether. There was thus obtained 7-chloro-4-(3'-chloro-4'-fluoroanilino)-6-nitroquinazoline hydrochloride (23.2 g);

NHR Spectrum: (CD$_3$SOCD$_3$) 7.50 (m, 1H), 7.82 (m, 1H), 8.14 (m, 1H), 8.18 (s, 1H), 8.88 (s, 1H), 9.67 (s, 1H), 11.3 (broad s, 1H);

Elemental Analysis: Found C, 43.9; H, 2.1; N, 14.5; C$_{14}$H$_8$N$_4$Cl$_2$F 0.8HCl requires C, 43.8; H, 2.3; N, 14.6%.

A mixture of a portion (10 g) of the quinazoline so obtained, an ethanolic solution of methylamine (33% weight/volume, 50 ml) and ethanol (100 ml) was stirred and heated to 70° C. for 5 hours under a condenser cooled with solid carbon dioxide. The mixture was allowed to stand at ambient temperature for 16 hours. The precipitate was isolated, washed with ethanol and with diethyl ether and dried. There was thus obtained 4-(3'-chloro-4'-fluoroanilino)-7-methylamino-6-nitroquinazoline (5.8 g);

NMR Spectrum: (CD$_3$SOCD$_3$) 2.99 (d, 3H), 6.89 (s, 1H), 7.43 (m, 1H), 7.81 (m, 1H), 7.96 (m, 1H), 8.16 (m, 1H), 8.49 (s, 1H), 9.45 (s, 1H), 10.2 (broad s, 1H).

A mixture of a portion (4.4 g) of the quinazoline so obtained, 10% palladium-on-charcoal catalyst (0.6 g), methylene chloride (150 ml) and ethanol (150 ml) was stirred under an atmosphere of hydrogen for 5 hours. The mixture was filtered and the filtrate was evaporated. The residue was dissolved in a mixture of methylene chloride (50 ml) and methanol (10 ml) and the solution was stood at ambient temperature for 3 hours. A precipitate was deposited. The mixture was filtered and the filtrate was evaporated. The residue from the filtrate was purified by column chromatography using a 19:1 mixture of methylene chloride and methanol as eluent. There was thus obtained 6-amino-4-(3'-chloro-4'-fluoroanilino)-7-methylaminoquinazoline (1.84 g), m.p. 244°–247° C.;

NMR Spectrum (CD$_3$SOCD$_3$) 2.87 (d, 3H), 5.16 (broad s, 2H), 5.97 (m, 1H), 6.55 (s, 1H), 7.28 (m, 2H), 7.36 (m, 1H), 8.16 (m, 1H), 8.31 (s, 1H), 9.25 (broad s, 1H);

Elemental Analysis: Found C, 53.7; H, 5.0; N, 19.0; C$_{15}$H$_{13}$N$_5$ClF 1.5CH$_3$OH requires C, 54.1; H, 5.2; N, 19.1%.

EXAMPLE 4

A mixture of 6-amino-4-(3'-chloro-4'-fluoroanilino)-7-methylaminoquinazoline (0.3 g) and trifluoroacetic acid (10 ml) was stirred and heated to reflux for 30 minutes. The mixture was cooled to ambient temperature and evaporated. The residue was triturated under dilute aqueous ammonium hydroxide solution. The residue was washed with water and dried. There was thus obtained 8-(3'-chloro-4'-fluoroanilino)-3-methyl-2-trifluoromethyl-3H-imidazo[4,5-g] quinazoline (0.182 g);

NMR Spectrum: (CD$_3$SOCD$_3$) 4.08 (s, 3H), 7.46 (t, 1H), 7.92 (m, 1H), 8.20 (s, 1H), 8.28 (m, 1H), 8.64 (s, 1H), 9.19 (s, 1H), 10.04 (broad s, 1H);

Elemental Analysis: Found C, 49.5; H, 2.4; N, 16.8; C$_{17}$H$_{10}$N$_5$ClF$_4$ 0.2CF$_3$CO$_2$H requires C, 49.9; H, 2.4; N, 16.7%.

EXAMPLE 5

A mixture of 6-amino-4-(3'-chloro-4'-fluoroanilino)-7-methylaminoquinazoline (0.3 g), tetraethyl orthocarbonate (2 ml) and acetic acid (0.07 ml) was stirred and heated to 100° C. for 2 hours. The mixture was cooled to ambient temperature. The precipitate was isolated, washed with diethyl ether and dried. There was thus obtained 8-(3'-chloro-4'-fluoroanilino)-2-ethoxy-3-methyl-3H-imidazo[4,5-g]-quinazoline (0.253 g);

NMR Spectrum: (CD$_3$SOCD$_3$) 1.47 (t, 3H), 3.64 (s, 3H), 4.65 (m, 2H), 7.37 (s, 1H), 7.43 (m, 1H), 7.92 (m, 1H), 8.32 (m, 1H), 8.56 (s, 1H), 8.60 (s, 1H), 9.67 (broad s, 1H);

Elemental Analysis: Found C, 58.3; H, 4.0; N, 18.9; C$_{18}$H$_{15}$N$_5$ClFO requires C, 58.1; H, 4.1; N, 18.8%.

EXAMPLE 6

A mixture of 6-amino-7-(3-dimethylaminopropylamino)-4-(3'-methylanilino)quinazoline (0.15 g) and formic acid (2 ml) was stirred and heated to reflux for 2 hours. The mixture was evaporated and the residue was triturated under diethyl ether. The resultant solid was filtered off and washed with diethyl ether. There was thus obtained 3-(3-dimethylaminopropyl)-8-(3'-methylanilino)-3H-imidazo[4,5-g]-quinazoline as a solid (0.14 g);

NMR Spectrum: (CD$_3$SOCD$_3$) 2.02 (m, 2H), 2.19 (s, 6H), 2.25 (t, 2H), 2.34 (s, 3H), 4.39 (t, 2H), 6.94 (d, 1H), 7.28 (m, 1H), 7.75 (m, 2H), 7.97 (s, 1H), 8.55 (s, 2H), 9.02 (s, 1H), 9.68 (broad s, 1H).

The 6-amino-7-(3-dimethylaminopropylamino)-4-(3'-methylanilino)quinazoline used as a starting material was obtained as follows:

A mixture of 7-chloro-4-(3'-methylanilino)-6-nitroquinazoline (1.2 g), 3-dimethylaminopropylamine (6 ml) and DMA (20 ml) was stirred and heated to 80° C. for 2 hours. The mixture was evaporated and the residue was triturated under water. The resultant solid was washed with water and dried. There was thus obtained 7-(3-dimethylaminopropylamino)-6-nitro-4-(3'-methylanilino)quinazoline (1.35 g) which was used without further purification.

A mixture of a portion (1 g) of the material so obtained, 10% palladium-on-charcoal catalyst (0.1 g) and ethanol (80 ml) was stirred and heated to 45° C. for 2 hours. The mixture was cooled to ambient temperature and filtered. The liltrate was evaporated. The residue was partitioned between ethyl acetate and 1N aqueous hydrochloric acid solution. The aqueous layer was basified by the addition of ammonium hydroxide solution and the mixture was extracted with ethyl acetate. The organic phase was dried (MgSO$_4$) and evaporated. There was thus obtained 6-amino-7-(3-dimethylaminopropylamino)-4-(3'-methylanilino)quinazoline as a foam (0.61 g), m.p. 60°–66° C.

EXAMPLE 7

A mixture of 6,7-diamino-4-(3'-chloro-4'-fluoroanilino) quinazoline (0.1 g), biacetyl (0.037 g) and ethanol (2 ml) was heated to reflux for 4 hours. The mixture was cooled to ambient temperature and the precipitate was isolated, washed with water and dried. There was thus obtained 4-(3'-chloro-4'-fluoroanilino)-7,8-dimethylpyrazino-[2,3-g] quinazoline (0.054 g), m.p. >270° C.;

NMR Spectrum: (CD$_3$SOCD$_3$) 2.77 (s, 6H), 7.49 (m, 1H), 7.92 (m, 1H), 8.26 (s, 1H), 8.35 (d, 1H), 8.70 (s, 1H), 9.37 (s, 1H), 10.27 (broad s, 1H).

The 6,7-diamino-4-(3'-chloro-4'-fluoroanilino)quinazoline used as a starting material was obtained as follows:

Sodium azide (0.509 g) was added portionwise to a stirred solution of 7-chloro-4-(3'-chloro-4'-fluoroanilino)-6-nitroquinazoline hydrochloride (1 g) in DMA (250 ml). The mixture was stirred and heated to 90° C. for 2 hours. A quantity (0.2 g) of 10% palladium-on-charcoal catalyst was added and the mixture was stirred under an atmosphere of hydrogen and heated to 80° C. for 2 hours. The mixture was cooled to ambient temperature and filtered. The filtrate was evaporated and the residue was purified by column chromatography using a 19:1 mixture of methylene chloride and methanol as eluent. There was thus obtained 6,7-diamino-4-(3'-chloro-4'-fluoroanilino)quinazoline as a solid (0.39 g), m.p. 254°–257° C.;

NMR Spectrum: (CD$_3$SOCD$_3$) 5.17 (broad s, 2H), 5.83 (broad s, 1H), 6.78 (s, 1H), 7.28 (s, 1H), 7.3 (broad s, 1H), 7.36 (m, 1H), 7.76 (m, 1H), 8.15 (m, 1H), 8.28 (s, 1H).

EXAMPLE 8

A mixture of 6-amino-4-(3'-chloro-4'-fluoroanilino)-7-methylaminoquinazoline (0.05 g), oxalic acid (0.075 g), water (1 ml) and acetic acid (1 ml) was stirred and heated to reflux for 3 hours. The mixture was evaporated and the residue was triturated with water. The resultant solid was washed with water and dried. There was thus obtained 4-(3'-chloro-4'-fluoroanilino)-7-hydroxy-9-methyl-8-oxo-8,9-dihydropyrazino[2,3-g]quinazoline (0.028 g);

NHR Spectrum: (CD$_3$SOCD$_3$) 3.62 (s, 3H), 7.43 (t, 1H), 7.63 (s, 1H), 7.75 (m, 1H), 7.99 (s, 1H), 8.10 (m, 1H), 8.59 (s, 1H), 10.0 (broad s, 1H), 11.9 (broad s, 1H).

CHEMICAL FORMULAE

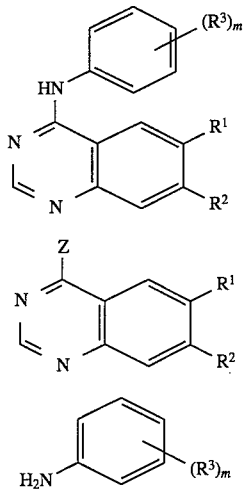

I

II

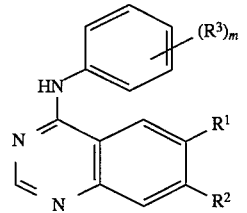

III

I claim:
1. A tricyclic derivative of the formula I

I wherein R$^1$ and R$^2$ together form a group of the formula —N=CH—NH—, —N=N—NH—, —NH—N=CH—, —NH—CO—NH—, —NH—NH—CO—, —N=N—CH=CH—, —N=CH—N=CH—, —N=CH—CH=N—, or —N=CH—CO—NH— (with in each case a nitrogen atom being located at the 6-position of the quinazoline ring) and the 5- or 6-membered ring so formed may optionally bear one or two substituents, any substituent on an available nitrogen atom being selected from (1–4C)alkyl, (3–4C)alkenyl, (3–4C)alkynyl, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-(i-4C)alkyl, (1–4C)alkylamino-(1–4C)alkyl and di-[(1–4C)alkyl]amino-(1–4C)alkyl, and any substituent on an available carbon atom being selected from halogeno, amino, hydroxy, carbamoyl, cyano, (1–4C)alkyl, (2–4C)alkenyl, (2–4C)alkynyl, (1–4C)alkoxy, (1–4C)alkylthio, (1–4C)alkylsulphinyl, (1–4C)alkylsulphonyl, (1–4C)alkylamino, di-[(1–4C)alkyl]amino, (2–4C)alkanoyl, N-(1–4C)alkylcarbamoyl, N,N-di-[(1–4C)alkyl]carbamoyl, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-(1–4C)alkyl, (1–4C)alkylamino-(1–4C)alkyl and di-[(1–4C)alkyl]amino-(1–4C)alkyl; and m is the integer 1, 2 or 3 and each R$^3$ is independently hydrogen, halogeno, trifluoromethyl, hydroxy, amino, nitro, cyano, (1–4C)alkyl, (1–4C)alkoxy, (1–4C)alkylamino, di-[(1–4C)alkyl]amino or (2–4C)alkanoylamino; or a pharmaceutically-acceptable salt thereof.

2. A tricyclic derivative of the formula I as claimed in claim 1 wherein the 6,6,5-tricyclic ring defined by the linking of the groups R$^1$ and R$^2$ is selected from 3H-imidazo [4,5-g]quinazolin-8-yl, 3H-[1,2,3]triazolo[4,5-g]quinazolin-8-yl, 1H-pyrazolo[3,4-g]quinazolin-8-yl, 6H-pyrrolo[2,3-g]quinazolin-4-yl, 3-oxo-2,3-dihydro-1H-pyrazolo[3,4-g]quinazolin-8-yl, and the 5-membered ring involving R$^1$ and R$^2$ may optionally bear one or two substituents, any substituent on an available nitrogen atom being selected from methyl, ethyl, propyl, allyl, prop-2-ynyl, 2,2,2-trifluoroethyl, 2-hydroxyethyl, 3-hydroxypropyl, 2-acetoxyethyl, 2-methoxyethyl, 3-methoxypropyl, cyanomethyl, 2-cyanoethyl, 2-aminoethyl, 2-methylaminoethyl and 2-dimethylaminoethyl, and any substituent on an available carbon atom being selected from fluoro, chloro, amino, carbamoyl, cyano, methyl, ethyl, propyl, vinyl, allyl, ethynyl, prop-2-ynyl, methoxy, ethoxy, propoxy, methylthio, methylsulphinyl, methylsulphonyl, methylamino, dimethylamino, acetyl, N-methylcarbamoyl, N,N-dimethylcarbamoyl, fluoromethyl, difluoromethyl, trifluoromethyl, 2,2,2-trifluoroethyl, hydroxymethyl, 2-hydroxyethyl, acetoxymethyl, 2-acetoxyethyl, methoxymethyl, 2-methoxyethyl, cyanomethyl, 2-cyanoethyl, aminomethyl, 2-aminoethyl, methylaminomethyl, 2-methylaminoethyl, dimethylaminomethyl and 2-dimethylaminoethyl; and m is the integer 1, 2 or 3 and each R$^3$ is independently hydrogen, fluoro, chloro, bromo, trifluoromethyl, hydroxy, amino, nitro, cyano, methyl, ethyl, methoxy, methylamino, dimethylamino or acetamido; or a pharmaceutically-acceptable salt thereof.

3. A tricyclic derivative of the formula I as claimed in claim 1 wherein the 6,6,6-tricyclic ring defined by the linking of the groups R$^1$ and R$^2$ is selected from pyrido[2,3-g]quinazolin-4-yl, pyrimidino[4,5-g]cinnolin-9-yl, pyrimidino[4,5-g]quinazolin-4-yl, pyrazino[2,3-g]quinazolin-4-yl, 7-oxo-6,7-dihydropyrido[2,3-g]quinazolin-4-yl and 8-oxo-8,9-dihydropyrazino[2,3-g]quinazolin-4-yl, and the 6-membered ring involving R$^1$ and R$^2$ may optionally bear one or two substituents, any substituent on an available nitrogen atom being selected from methyl, ethyl and propyl, and any substituent on an available carbon atom being selected from fluoro, chloro, hydroxy, carbamoyl, cyano, methyl, methoxy, ethoxy, N-methylcarbamoyl, N,N-dimethylcarbamoyl, trifluoromethyl and 2,2,2-trifluoroethyl; and m is the integer 1 or 2 and each R$^3$ is independently hydrogen, fluoro, chloro, bromo, trifluoromethyl, nitro, cyano, methyl or ethyl; or a pharmaceutically-acceptable salt thereof.

4. A tricyclic derivative of the formula I as claimed in claim 1 wherein the 6,6,5-tricyclic ring defined by the linking of the groups R$^1$ and R$^2$ is selected from 3-methyl-3H-imidazo[4,5-g]quinazolin-8-yl, 3-methyl-3H-[1,2,3]triazolo[4,5-g]quinazolin-8-yl and 3-methyl-2-oxo-1,2-dihydro-3H-imidazo[4,5-g]quinazolin-8-yl; and (R$^3$)$_m$ is 3'-methyl, 3'-chloro or 3'-chloro-4'-fluoro; or a pharmaceutically-acceptable salt thereof.

5. A tricyclic derivative of the formula I as claimed in claim 1 wherein the 6,6,5-tricyclic ring defined by the linking of the groups R$^1$ and R$^2$ is selected from 3-methyl-3H-imidazo[4,5-g]quinazolin-8-yl, 3-methyl-2-oxo-1,2-dihydro-3H-imidazo[4,5-g]quinazolin-8-yl and 3-methyl-2-trifluoromethyl-3H-imidazo[4,5-g]quinazolin-8-yl; and (R$^3$)$_m$ is 3'-methyl, 3'-chloro or 3'-chloro-4'-fluoro; or a pharmaceutically-acceptable salt thereof.

6. A tricyclic derivative of the formula I as claimed in claim 1 wherein the 6,6,6-tricyclic ring defined by the linking of the groups R$^1$ and R$^2$ is selected from 7,8-dimethylpyrazino[2,3-g]quinazolin-4-yl and 7-hydroxy-9-methyl-8-oxo-8,9-dihydropyrazino[2,3-g]quinazolin-4-yl; and (R$^3$)$_m$ is 3'-methyl, 3'-chloro or 3'-chloro-4'-fluoro; or a pharmaceutically-acceptable salt thereof.

7. A tricyclic derivative of the formula I as claimed in claim 1 selected from:

3-methyl-8-(3'-methylanilino)-3H-imidazo[4,5-g]quinazoline, 3-methyl-8-(3'-methylanilino)-1,2-dihydro-3H-imidazo[4,5-g]quinazolin-2-one and 8-(3'-chloro-4'-fluoroanilino)-3-methyl-2-trifluoromethyl-3H-imidazo-[4,5-g]quinazoline;

or a pharmaceutically-acceptable salt thereof.

8. A tricyclic derivative of the formula I as claimed in claim 1 selected from:

4-(3'-chloro-4'-fluoroanilino)-7,8-dimethylpyrazino[2,3-g]quinazoline and 4-(3'-chloro-4'-fluoroanilino)-7-hydroxy-9-methyl-8-oxo-8,9-dihydro-pyrazino[2,3-g]quinazoline;

or a pharmaceutically-acceptable salt thereof.

9. A tricyclic derivative of the formula I as claimed in claim 1 wherein $R^1$ and $R^2$ together form a group of the formula —N=CH—NH—, —N=N—NH—, —NH—CO—NH—, —N=CH—CH=N— or —N=CH—CO—NH—; or a pharmaceutically-acceptable salt thereof.

10. A tricyclic derivative of the formula I as claimed in claim 2 wherein the 6,6,5-tricyclic ring defined by the linking of the groups $R^1$ and $R^2$ is selected from 3H-imidazo[4,5-g]quinazolin-8-yl, 3H-[1,2,3]triazolo[4,5-g]quinazolin-8-yl and -oxo-1,2-dihydro-3H-imidazo[4,5-g]quinazolin-8-yl; or a pharmaceutically-acceptable salt thereof.

11. A pharmaceutical composition which comprises a tricyclic derivative of the formula I, or a pharmaceutically-acceptable salt thereof, as claimed in any one of claims 1 to 8 in association with a pharmaceutically-acceptable diluent or carrier.

12. A method for producing an anti-cancer effect in a warm-blooded animal having a cancer which is sensitive to inhibition of the EGF-type of receptor tyrosine kinase enzymes which comprises administering to said animal an effective amount of a tricyclic derivative of the formula I, or a pharmaceutically-acceptable salt thereof, as claimed in any one of claims 3 to 10.

13. A method for producing an anti-proliferative effect in a warm-blooded animal having a cancer which is sensitive to inhibition of the EGF-type of receptor tyrosine kinase enzymes which comprises administering to said animal an effective amount of a tricyclic derivative of the formula I, or a pharmaceutically-acceptable salt thereof, as claimed in any one of claims 3 to 10.

14. A method for aiding the regression or palliation in a warm-blooded animal of a cancer which is sensitive to inhibition of the EGF-type of receptor tyrosine kinase enzymes which comprises administering to said animal an effective amount of a tricyclic derivative of the formula I, or a pharmaceutically-acceptable salt thereof, as claimed in any one of claims 3 to 10.

15. A method for producing in a warm-blooded animal an inhibitory effect against the EGF-type of receptor tyrosine kinase enzymes which comprises administering to said animal an effective amount of a tricyclic derivative of the formula I, or a pharmaceutically-acceptable salt thereof, as claimed in any one of claims 3 to 10.

* * * * *